United States Patent
Conejo-Garcia et al.

(10) Patent No.: US 8,084,217 B2
(45) Date of Patent: Dec. 27, 2011

(54) CD161 LIGAND, PILAR, FOR MODULATING ACTIVATION AND PROLIFERATION OF T CELLS

(75) Inventors: Jose R. Conejo-Garcia, East Thetford, VT (US); Eduardo Huarte-Sobrino, Bozeman, MT (US); Juan Cubillos-Ruiz, Lebanon, NH (US); Yolanda Nesbeth, Lebanon, NH (US); Diana G. Martinez, White River Junction, VT (US)

(73) Assignee: Trustees of Dartmouth College, Hanover, NH (US)

( * ) Notice: Subject to any disclaimer, the term of this patent is extended or adjusted under 35 U.S.C. 154(b) by 139 days.

(21) Appl. No.: 12/595,093

(22) PCT Filed: Apr. 10, 2008

(86) PCT No.: PCT/US2008/059879
§ 371 (c)(1),
(2), (4) Date: Oct. 8, 2009

(87) PCT Pub. No.: WO2008/127973
PCT Pub. Date: Oct. 23, 2008

(65) Prior Publication Data
US 2010/0143363 A1 Jun. 10, 2010

Related U.S. Application Data

(60) Provisional application No. 61/015,864, filed on Dec. 21, 2007, provisional application No. 60/911,138, filed on Apr. 11, 2007.

(51) Int. Cl.
*G01N 33/53* (2006.01)
(52) U.S. Cl. .......................................................... 435/7.1
(58) Field of Classification Search ........................ None
See application file for complete search history.

(56) References Cited

OTHER PUBLICATIONS

Exley et al., J. Exp. Med., 1998, 188: 867-876.*
NCBI entry CLC2A_HUMAN (2011), 5 pages.*
Aldemir et al. "Cutting Edge: Lectin-Like Transcript 1 Is a Ligand for the CD161 Receptor" The Journal of Immunology 2005 vol. 175(2) 7791-7795.
Benencia et al. "CLEC2A2 is a Novel Regulatory Immunoreceptor" Abstract presented at New England Immunology Conference, Oct. 2006.
NCBI Accession No. EF127467 (Huarte-Sobrino et al.) Nov. 2, 2006.
NCBI Accession No. NM 207375 (Clark et al.) 2003.
NCBI Accession No. AAQ89483 (Clark, H.F.) Dec. 2003.

* cited by examiner

*Primary Examiner* — Ilia Ouspenski
(74) *Attorney, Agent, or Firm* — Licata & Tyrrell P.C.

(57) ABSTRACT

The invention relates to a CD161 ligand known as Proliferation-Induced Lymphocyte-Associated Receptor (PILAR), which is crucial for a robust expansion of human lymphocytes. PILAR is markedly up-regulated on both CD4 and CD8 T cells upon TCR engagement and increases the expression of anti-apoptotic genes and glucose transporters through CD161, which globally results in a dramatic enhancement of T cell proliferation. Agents which stimulate or block this activity are also provided as are methods for manipulating PILAR signaling in the treatment of disease.

1 Claim, 6 Drawing Sheets

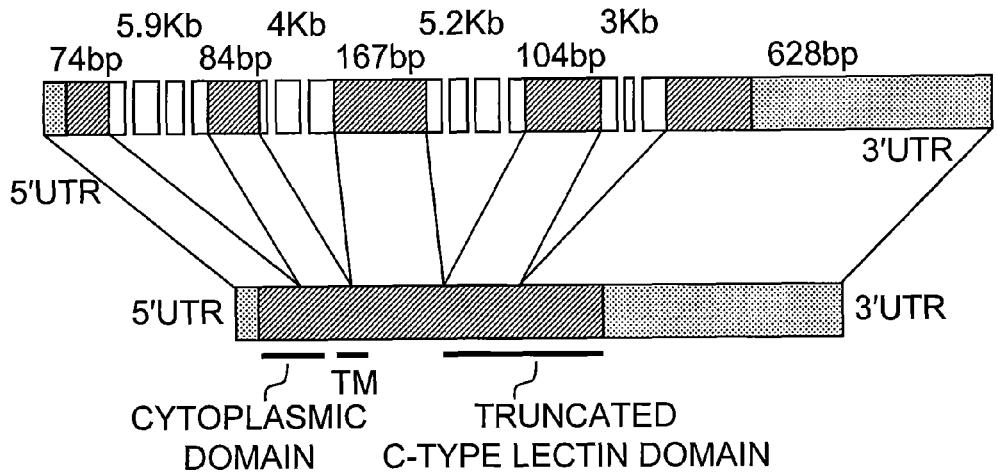

FIG. 1A

```
PILAR    --------------MINP-ELRD--GRADGFIHRIVPKLIQNWKIGLMCF
CLEC2D   -----MHDSNNVEKDITPSELPANPGCLHSKEHSIKATLIWRLFF-LIMF
CD69     MSSENCFVAENSSLHPESGQENDATSPHFSTRHEGSFQVPVLCAVMNVVF

PILAR    LSIIITTVCIIMIATWS-----KHAKP-----VACSGDWLGVRDKCFYFS
CLEC2D   LTIIVCGMVAALSAIRAN----CHQEPSVCLQAACPESWIGFQRKCFYFS
CD69     ITILIIALIALSVGQYNCPGQYTFSMPSDSHVSSCSEDWVGYQRKCYFIS

PILAR    DDTRNWTASKIFCSLQKAELAQIDTQEDMEFLKRYAGTDMHWIGLSRKQG
CLEC2D   DDTKNWTSSQRFCDSQDADLAQVESFQELNFLLRYKGPSDHWIGLSREQG
CD69     TVKRSWTSAQNACSEHGATLAVIDSEKDMNFLKRYAGREEHWVGLKKEPG

PILAR    DSWKWINGTTFNGWFEIIGNGSFAFLSADGVHSSRGFIDIKWICSKPKYF
CLEC2D   QPWKWINGTEWTRQFPILGAGECAYLNDKGASSARHYTERKWICSKSDIH
CD69     HPWKWSNGKEFNNWFNVTGSDKCVFLKNTEVSSMECEKNLYWICNKPYK-

PILAR    L   174  (SEQ ID NO:1)
CLEC2D   V   191  (SEQ ID NO:3)
CD69     -   199  (SEQ ID NO:2)
```

FIG. 1B

```
CLEC2A    MINPELRDGRADGFIHRIVPKLIQNWKIGLMCFLSIIITTVCIIMIATW
INPE5792  MINPELRDGRADGFIHRIVPKLIQNWKIGLMCFLSIIITTVCIIMIATW
PILAR     MINPELRDGRADGFIHRIVPKLIQNWKIGLMCFLSIIITTVCIIMIATW
          *************************************************

CLEC2A    SKHAKPVACSGDWLGVRDKCFYFSDDTRNWTASKIFCSLQKAELAQIDT
INPE5792  SKHAKPVACSGDWLGVRDKCFYFSDDTRNWTASKIFCSLQKAELAQIDT
PILAR     SKHAKPVACSGDWLGVRDKCFYFSDDTRNWTASKIFCSLQKAELAQIDT
          *************************************************

CLEC2A    QEDMEFLKRYAGTDMHWIGLSRKQGDSWKWTNGTTFNGWP------SNS
INPE5792  QEDMEFLKRYAGTDMHWIGLSRKQGDSWKWTNGTTFNGWP------SNS
PILAR     QEDMEFLKRYAGTDMHWIGLSRKQGDSWKWTNGTTFNGWFEIIGNGSFA
          ***************************************       * :

CLEC2A    KWSCN--WSLR-----QWLLLLGPLR- 160 (SEQ ID NO:5)
INPE5792  KWSCN--WSLR-----QWLLLLGPLR- 160 (SEQ ID NO:4)
PILAR     FLSADGVHSSRGFIDIKWICSKPKYFL 174 (SEQ ID NO:1)
          *.:    * *       :*:
```

FIG. 1C

```
tgaaaagctttctagtcctctcctactgatctccatcggttagcgccttgccatgatt
                                                          M  I
aatccagagctgcgggatggcagagctgatggcttcatacatcggatagttcccaag
 N  P  E  L  R  D  G  R  A  D  G  F  I  H  R  I  V  P  K ttgatacaaaactggaagattggccttatgtgcttcctgagtattattattactaca
 L  I  Q  N  W  K  I  G  L  M  C  F  L  S  I  I  I  T  T gtttgcattattatgatagccacatggtccaagcatgctaaacctgtggcatgttca
 V  C  I  I  M  I  A  T  W  S  K  H  A  K  P  V  A  C  S ggggactggcttggagtgagagataagtgtttctattttctgatgataccagaaat
 G  D  W  L  G  V  R  D  K  C  F  Y  F  S  D  D  T  R  N tggacagccagtaaaatattttgtagtttgcagaaagcagaacttgctcagattgat
 W  T  A  S  K  I  F  C  S  L  Q  K  A  E  L  A  Q  I  D acacaagaagacatggaattttgaagaggtacgcaggaactgatatgcactggatt
 T  Q  E  D  M  E  F  L  K  R  Y  A  G  T  D  M  H  W  I ggactaagcaggaaacaaggagattcttggaaatggacaaatggcaccacattcaat
 G  L  S  R  K  Q  G  D  S  W  K  W  T  N  G  T  T  F  N ggttggtttgaaattatagggaacggatcctttgctttcttgagtgctgatggagtc
 G  W  F  E  I  I  G  N  G  S  F  A  F  L  S  A  D  G  V catagttccagaggatttattgatatcaagtggatttgcagcaaacctaaatatttt
 H  S  S  R  G  F  I  D  I  K  W  I  C  S  K  P  K  Y  F ttatagagcagaaaaaacttgaaaatgattatcacacttcaagattgaaagaagagc
 L  - taattatgcaaaagtggctttctcacttattctgttacagaatacggaacctctggt
gagggcccattttctagtttatagatggaaacttcttgctgtgccctgccatggtta
aagagacaaggccgttctctggagccttttataagggcacaatcacatttactatgg
ctccatcctcatgaactaatcacctcctgatggatggctccatcccctaataccatc
acactggtgattagctttcaatttatgagttttggggagacccaaatactcagaaca
tag
```

*FIG. 1D*

SEQUENCE LISTING

```
<160> NUMBER OF SEQ ID NOS: 26

<210> SEQ ID NO 1
<211> LENGTH: 174
<212> TYPE: PRT
<213> ORGANISM: Homo sapiens

<400> SEQUENCE: 1

Met Ile Asn Pro Glu Leu Arg Asp Gly Arg Ala Asp Gly Phe Ile His
1               5                   10                  15

Arg Ile Val Pro Lys Leu Ile Gln Asn Trp Lys Ile Gly Leu Met Cys
            20                  25                  30
```

```
Phe Leu Ser Ile Ile Thr Thr Val Cys Ile Ile Met Ile Ala Thr
            35                  40                  45

Trp Ser Lys His Ala Lys Pro Val Ala Cys Ser Gly Asp Trp Leu Gly
 50                  55                  60

Val Arg Asp Lys Cys Phe Tyr Phe Ser Asp Thr Arg Asn Trp Thr
 65                  70                  75                  80

Ala Ser Lys Ile Phe Cys Ser Leu Gln Lys Ala Glu Leu Ala Gln Ile
                     85                  90                  95

Asp Thr Gln Glu Asp Met Glu Phe Leu Lys Arg Tyr Ala Gly Thr Asp
                100                 105                 110

Met His Trp Ile Gly Leu Ser Arg Lys Gln Gly Asp Ser Trp Lys Trp
            115                 120                 125

Ile Asn Gly Thr Thr Phe Asn Gly Trp Phe Glu Ile Ile Gly Asn Gly
            130                 135                 140

Ser Phe Ala Phe Leu Ser Ala Asp Gly Val His Ser Ser Arg Gly Phe
145                 150                 155                 160

Ile Asp Ile Lys Trp Ile Cys Ser Lys Pro Lys Tyr Phe Leu
                    165                 170
```

<210> SEQ ID NO 2
<211> LENGTH: 199
<212> TYPE: PRT
<213> ORGANISM: Homo sapiens

<400> SEQUENCE: 2

```
Met Ser Ser Glu Asn Cys Phe Val Ala Glu Asn Ser Ser Leu His Pro
 1               5                  10                  15

Glu Ser Gly Gln Glu Asn Asp Ala Thr Ser Pro His Phe Ser Thr Arg
             20                  25                  30

His Glu Gly Ser Phe Gln Val Pro Val Leu Cys Ala Val Met Asn Val
            35                  40                  45

Val Phe Ile Thr Ile Leu Ile Ile Ala Leu Ile Ala Leu Ser Val Gly
 50                  55                  60

Gln Tyr Asn Cys Pro Gly Gln Tyr Thr Phe Ser Met Pro Ser Asp Ser
 65                  70                  75                  80

His Val Ser Ser Cys Ser Glu Asp Trp Val Gly Tyr Gln Arg Lys Cys
                     85                  90                  95

Tyr Phe Ile Ser Thr Val Lys Arg Ser Trp Thr Ser Ala Gln Asn Ala
                100                 105                 110

Cys Ser Glu His Gly Ala Thr Leu Ala Val Ile Asp Ser Glu Lys Asp
            115                 120                 125

Met Asn Phe Leu Lys Arg Tyr Ala Gly Arg Glu Glu His Trp Val Gly
            130                 135                 140

Leu Lys Lys Glu Pro Gly His Pro Trp Lys Trp Ser Asn Gly Lys Glu
145                 150                 155                 160

Phe Asn Asn Trp Phe Asn Val Thr Gly Ser Asp Lys Cys Val Phe Leu
                    165                 170                 175

Lys Asn Thr Glu Val Ser Ser Met Glu Cys Glu Lys Asn Leu Tyr Trp
                180                 185                 190

Ile Cys Asn Lys Pro Tyr Lys
            195
```

<210> SEQ ID NO 3
<211> LENGTH: 191
<212> TYPE: PRT
<213> ORGANISM: Homo sapiens

<400> SEQUENCE: 3

```
Met His Asp Ser Asn Asn Val Glu Lys Asp Ile Thr Pro Ser Glu Leu
1               5                   10                  15

Pro Ala Asn Pro Gly Cys Leu His Ser Lys Glu His Ser Ile Lys Ala
            20                  25                  30

Thr Leu Ile Trp Arg Leu Phe Phe Leu Ile Met Phe Leu Thr Ile Ile
        35                  40                  45

Val Cys Gly Met Val Ala Ala Leu Ser Ala Ile Arg Ala Asn Cys His
50                  55                  60

Gln Glu Pro Ser Val Cys Leu Gln Ala Ala Cys Pro Glu Ser Trp Ile
65                  70                  75                  80

Gly Phe Gln Arg Lys Cys Phe Tyr Phe Ser Asp Asp Thr Lys Asn Trp
            85                  90                  95

Thr Ser Ser Gln Arg Phe Cys Asp Ser Gln Asp Ala Asp Leu Ala Gln
            100                 105                 110

Val Glu Ser Phe Gln Glu Leu Asn Phe Leu Arg Tyr Lys Gly Pro
        115                 120                 125

Ser Asp His Trp Ile Gly Leu Ser Arg Glu Gln Gly Gln Pro Trp Lys
130                 135                 140

Trp Ile Asn Gly Thr Glu Trp Thr Arg Gln Phe Pro Ile Leu Gly Ala
145                 150                 155                 160

Gly Glu Cys Ala Tyr Leu Asn Asp Lys Gly Ala Ser Ser Ala Arg His
            165                 170                 175

Tyr Thr Glu Arg Lys Trp Ile Cys Ser Lys Ser Asp Ile His Val
        180                 185                 190
```

<210> SEQ ID NO 4
<211> LENGTH: 160
<212> TYPE: PRT
<213> ORGANISM: Homo sapiens

<400> SEQUENCE: 4

```
Met Ile Asn Pro Glu Leu Arg Asp Gly Arg Ala Asp Gly Phe Ile His
1               5                   10                  15

Arg Ile Val Pro Lys Leu Ile Gln Asn Trp Lys Ile Gly Leu Met Cys
            20                  25                  30

Phe Leu Ser Ile Ile Ile Thr Thr Val Cys Ile Met Ile Ala Thr
        35                  40                  45

Trp Ser Lys His Ala Lys Pro Val Ala Cys Ser Gly Asp Trp Leu Gly
50                  55                  60

Val Arg Asp Lys Cys Phe Tyr Phe Ser Asp Asp Thr Arg Asn Trp Thr
65                  70                  75                  80

Ala Ser Lys Ile Phe Cys Ser Leu Gln Lys Ala Glu Leu Ala Gln Ile
            85                  90                  95

Asp Thr Gln Glu Asp Met Glu Phe Leu Lys Arg Tyr Ala Gly Thr Asp
            100                 105                 110

Met His Trp Ile Gly Leu Ser Arg Lys Gln Gly Asp Ser Trp Lys Trp
        115                 120                 125

Thr Asn Gly Thr Thr Phe Asn Gly Trp Pro Ser Asn Ser Lys Trp Ser
        130                 135                 140

Cys Asn Trp Ser Leu Arg Gln Trp Leu Leu Leu Gly Pro Leu Arg
145                 150                 155                 160
```

<210> SEQ ID NO 5
<211> LENGTH: 160
<212> TYPE: PRT

<213> ORGANISM: Homo sapiens

<400> SEQUENCE: 5

```
Met Ile Asn Pro Glu Leu Arg Asp Gly Arg Ala Asp Gly Phe Ile His
1               5                   10                  15
Arg Ile Val Pro Lys Leu Ile Gln Asn Trp Lys Ile Gly Leu Met Cys
            20                  25                  30
Phe Leu Ser Ile Ile Ile Thr Thr Val Cys Ile Met Ile Ala Thr
        35                  40                  45
Trp Ser Lys His Ala Lys Pro Val Ala Cys Ser Gly Asp Trp Leu Gly
    50                  55                  60
Val Arg Asp Lys Cys Phe Tyr Phe Ser Asp Asp Thr Arg Asn Trp Thr
65                  70                  75                  80
Ala Ser Lys Ile Phe Cys Ser Leu Gln Lys Ala Glu Leu Ala Gln Ile
                85                  90                  95
Asp Thr Gln Glu Asp Met Glu Phe Leu Lys Arg Tyr Ala Gly Thr Asp
            100                 105                 110
Met His Trp Ile Gly Leu Ser Arg Lys Gln Gly Asp Ser Trp Lys Trp
        115                 120                 125
Thr Asn Gly Thr Thr Phe Asn Gly Trp Pro Ser Asn Ser Lys Trp Ser
    130                 135                 140
Cys Asn Trp Ser Leu Arg Gln Trp Leu Leu Leu Gly Pro Leu Arg
145                 150                 155                 160
```

<210> SEQ ID NO 6
<211> LENGTH: 916
<212> TYPE: DNA
<213> ORGANISM: Homo sapiens

<400> SEQUENCE: 6

```
tgaaaagctt tctagtcctc tcctactgat ctccatcggt tagcgccttg ccatgattaa     60
tccagagctg cgggatggca gagctgatgg cttcatacat cggatagttc ccaagttgat    120
acaaaactgg aagattggcc ttatgtgctt cctgagtatt attattacta cagtttgcat    180
tattatgata gccacatggt ccaagcatgc taaacctgtg gcatgttcag gggactggct    240
tggagtgaga gataagtgtt tctattttc tgatgatacc agaaattgga cagccagtaa    300
aatattttgt agtttgcaga aagcagaact tgctcagatt gatacacaag aagacatgga    360
atttttgaag aggtacgcag gaactgatat gcactggatt ggactaagca ggaaacaagg    420
agattcttgg aaatggacaa atggcaccac attcaatggt tggttgaaa ttataggaa     480
cggatccttt gctttcttga gtgctgatgg agtccatagt tccagaggat ttattgatat    540
caagtggatt tgcagcaaac ctaaatattt tttatagagc agaaaaaact tgaaaatgat    600
tatcacactt caagattgaa agaagagcta attatgcaaa agtggctttc tcacttattc    660
tgttacagaa tacggaacct ctggtgaggg cccattttct agtttataga tggaaacttc    720
ttgctgtgcc ctgccatggt taaagagaca aggccgttct ctggagcctt ttataagggc    780
acaatcacat ttactatggc tccatcctca tgaactaatc acctcctgat ggatggctcc    840
atcccctaat accatcacac tggtgattag ctttcaattt atgagttttg gaggaccca    900
aatactcaga acatag                                                    916
```

<210> SEQ ID NO 7
<211> LENGTH: 30
<212> TYPE: PRT
<213> ORGANISM: Artificial sequence
<220> FEATURE:

-continued

```
<223> OTHER INFORMATION: Synthetic peptide
<220> FEATURE:
<221> NAME/KEY: MISC_FEATURE
<222> LOCATION: (3)..(4)
<223> OTHER INFORMATION: Xaa denotes any amino acid residue
<220> FEATURE:
<221> NAME/KEY: MISC_FEATURE
<222> LOCATION: (6)..(7)
<223> OTHER INFORMATION: Xaa denotes any amino acid residue
<220> FEATURE:
<221> NAME/KEY: MISC_FEATURE
<222> LOCATION: (10)..(12)
<223> OTHER INFORMATION: Xaa denotes any amino acid residue
<220> FEATURE:
<221> NAME/KEY: MISC_FEATURE
<222> LOCATION: (15)..(16)
<223> OTHER INFORMATION: Xaa denotes any amino acid residue
<220> FEATURE:
<221> NAME/KEY: MISC_FEATURE
<222> LOCATION: (18)..(22)
<223> OTHER INFORMATION: Xaa denotes any amino acid residue
<220> FEATURE:
<221> NAME/KEY: MISC_FEATURE
<222> LOCATION: (24)..(25)
<223> OTHER INFORMATION: Xaa denotes any amino acid residue
<220> FEATURE:
<221> NAME/KEY: MISC_FEATURE
<222> LOCATION: (27)..(29)
<223> OTHER INFORMATION: Xaa denotes any amino acid residue

<400> SEQUENCE: 7

Cys Pro Xaa Xaa Trp Xaa Xaa Tyr Phe Xaa Xaa Xaa Cys Tyr Xaa Xaa
1               5                   10                  15

Ser Xaa Xaa Xaa Xaa Xaa Trp Xaa Xaa Ser Xaa Xaa Xaa Cys
            20                  25                  30

<210> SEQ ID NO 8
<211> LENGTH: 29
<212> TYPE: PRT
<213> ORGANISM: Homo sapiens

<400> SEQUENCE: 8

Cys Ser Gly Asp Trp Leu Gly Val Arg Asp Lys Cys Phe Tyr Phe Ser
1               5                   10                  15

Asp Asp Thr Arg Asn Trp Thr Ala Ser Lys Ile Phe Cys
            20                  25

<210> SEQ ID NO 9
<211> LENGTH: 37
<212> TYPE: PRT
<213> ORGANISM: Homo sapiens

<400> SEQUENCE: 9

Phe Glu Ile Ile Gly Asn Gly Ser Phe Ala Phe Leu Ser Ala Asp Gly
1               5                   10                  15

Val His Ser Ser Arg Gly Phe Ile Asp Ile Lys Trp Ile Cys Ser Lys
            20                  25                  30

Pro Lys Tyr Phe Leu
        35

<210> SEQ ID NO 10
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 10
caggggactg gcttggagtg agagat                                          26
```

-continued

<210> SEQ ID NO 11
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 11
tctgatgata ccagaaattg gacagccagt                                    30

<210> SEQ ID NO 12
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 12
atgggccctc accagaggtt ccgtat                                        26

<210> SEQ ID NO 13
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 13
tgctgcaaat ccacttgata tcaataaa                                      28

<210> SEQ ID NO 14
<211> LENGTH: 20
<212> TYPE: PRT
<213> ORGANISM: Homo sapiens

<400> SEQUENCE: 14

Ser Phe Ala Phe Leu Ser Ala Asp Gly Val His Ser Ser Arg Gly Phe
1               5                   10                  15

Ile Asp Ile Lys
            20

<210> SEQ ID NO 15
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 15
gttagcgcct tgccatgatt a                                             21

<210> SEQ ID NO 16
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 16
aggaagcaca taaggccaat ctt                                           23

<210> SEQ ID NO 17
<211> LENGTH: 33
<212> TYPE: DNA
<213> ORGANISM: Artificial sequence

```
<220> FEATURE:
<223> OTHER INFORMATION: Synthetic oligonucleotide

<400> SEQUENCE: 17
cttcatacat cggatagttc ccaagttgat aca                                    33

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
cctgcaccac caactgctta                                                   20

<210> SEQ ID NO 19
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 19
catgagtcct tccacgatac ca                                                22

<210> SEQ ID NO 20
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 20
cctggccaag gtcatccatg acaac                                             25

<210> SEQ ID NO 21
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 21
aagcttaagc atgctaaacc tgtggcatgt tc                                     32

<210> SEQ ID NO 22
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 22
gaattcaaaa tatttaggtt tgctgcaaat c                                      31

<210> SEQ ID NO 23
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 23
aagcttatac agaaatcatc aatagaaaaa tgc                                    33
```

```
<210> SEQ ID NO 24
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 24
ggatccgagt caggatacac tttatttctc aca                            33

<210> SEQ ID NO 25
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 25
aagcttcagt tttctgtgct tggac                                     25

<210> SEQ ID NO 26
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 26
gaattctctg ggcgctcctg aagaag                                    26
```

CD161 LIGAND, PILAR, FOR MODULATING ACTIVATION AND PROLIFERATION OF T CELLS

INTRODUCTION

This application is a National Stage Application of International Application No. PCT/US2008/059879 filed Apr. 10, 2008, which claims benefit of priority to U.S. Provisional Patent Application Ser. Nos. 60/911,138, filed Apr. 11, 2007, and 61/015,864, filed Dec. 21, 2007, the contents of which are incorporated herein by reference in their entireties.

This invention was made in the course of research sponsored by the National Center for Research Resources (Grant No. 2P20RR016437-06). The U.S. government may have certain rights in this invention.

BACKGROUND OF THE INVENTION

T cells are activated by engagement of their T cell receptor (TCR) by specific MHC-peptide complexes expressed on antigen-presenting cells, but other signals concurrently delivered decide the appropriate immune response. CD28 represents the archetype of activating costimulatory receptor (Carreno & Collins (2002) *Annu. Rev. Immunol.* 20:29-53; June, et al. (1987) *Mol. Cell. Biol.* 7:4472-4481; Thompson, et al. (1989) *Proc. Natl. Acad. Sci. USA* 86:1333-1337), but many other molecules contribute to support continued expansion and differentiation of T cells (Watts (2005) *Annu. Rev. Immunol.* 23:23-68; Markiewicz, et al. (2005) *J. Immunol.* 175: 2825-2833; Groh, et al. (2001) *Nat. Immunol.* 2:255-260; Conejo-Garcia, et al. (2004) *Cancer Res.* 64:2175-2182; Conejo-Garcia, et al. (2003) *Cancer Biol. Ther.* 2:446-451; Kahn & Koretzky (2006) *Nat. Immunol.* 7:1286-1288). In this context, the extent of naïve T cell proliferation is critically dependent on the cytokine milieu (Swain (1995) *J. Leukoc. Biol.* 57:795-798; Boyman, et al. (2006) *Science* 311:1924-1927).

Experimental results indicate that engagement of CD161, a C-type lectin receptor associated with NK cells (Lanier, et al. (1994) *J. Immunol.* 153:2417-2428), enhances IFN-γ and TNF-α production in the context of a TCR signal (Takahashi, et al. (2006) *J. Immunol.* 176:211-216; Aldemir, et al. (2005) *J. Immunol.* 175:7791-7795), while inducing the production of IL-12 by dendritic cells (Poggi, et al. (1997) *Eur. J. Immunol.* 27:2965-2970). Unlike murine lymphocytes, the expression of CD161 in human T cells identifies mostly memory lymphocytes, but only a small proportion of invariant NK T cells (Takahashi, et al. (2006) supra). The only previously identified ligand of CD161 is CLEC2D/LLT1 (Aldemir, et al. (2005) supra; Rosen, et al. (2005) *J. Immunol.* 175:7796-7799), another C-type lectin molecule mapping in the vicinity of NKG2D at the NK cluster. This narrow region of human chromosome 12 spans ~2 Mb and contains at least 18 different genes involved in immune responses that encode for leukocyte receptors exhibiting a C-type lectin-like motif in their extracellular part.

SUMMARY OF THE INVENTION

The present invention is an isolated nucleic acid molecule, wherein said nucleic acid molecule (a) encodes a Proliferation-Induced Lymphocyte-Associated Receptor (PILAR) polypeptide comprising the amino acid sequence set forth in SEQ ID NO:9; or (b) hybridizes to a nucleic acid molecule encoding a PILAR polypeptide comprising the amino acid sequence set forth in SEQ ID NO:9. In some embodiments, a vector harbors the nucleic acid molecule. In another embodiment, the vector is in a host cell.

The present invention is also an isolated PILAR polypeptide containing the amino acid sequence set forth in SEQ ID NO:9. In some embodiments, the PILAR polypeptide is in a host cell. In other embodiments, the PILAR polypeptide is in admixture with a pharmaceutically acceptable carrier.

The present invention is also an antibody which specifically binds to an isolated PILAR polypeptide.

A method for identifying an agent which modulates an activity of PILAR is also embraced by this invention. Such a screening assay involves contacting a PILAR polypeptide, or host cell expressing a PILAR polypeptide, with a test agent and determining whether the test agent modulates an activity of PILAR wherein a decrease in a PILAR activity is indicative of an agent which antagonizes PILAR and an increase in PILAR activity is indicative of an agent which agonizes PILAR.

Agents identified in accordance with this screening assay find application in methods for modulating T cell activation or proliferation, and methods for modulating immune responses in a subject. Subjects benefiting from such treatment include those with cancer, an autoimmune disease or inflammation.

BRIEF DESCRIPTION OF THE DRAWINGS

FIG. 1 shows the gene structure and amino acid sequence of PILAR. As depicted in FIG. 1A, the PILAR gene spans five exons encoding a predicted transmembrane molecule that exhibits a truncated C-type Lectin domain in the extracellular region. FIG. 1B shows the alignment of PILAR (SEQ ID NO:1) with two closely-related human molecules, namely the leukocyte markers CD69 (SEQ ID NO:2) and CLEC2D (SEQ ID NO:3). Sequence identity is indicated with "*". FIG. 1C shows the amino acid sequence alignment of PILAR (SEQ ID NO:1), INPE5792 (SEQ ID NO:4) and CLEC2A (SEQ ID NO:5). FIG. 1D shows the nucleic acid (SEQ ID NO:6) and deduced amino acid (SEQ ID NO:1) sequence for PILAR. Normal font represents the predicted intracellular domain; italic represents the predicted transmembrane domain; single underlining represents the predicted extracellular domain; and double underlining shows the location of a truncated C-type Lectin domain.

FIG. 3 shows that the expression of both PILAR and CD161 can be recovered on tumor-associated cytotoxic T cells ex vivo by activation with aAPCs. These results are representative of at least 2 independent experiments.

DETAILED DESCRIPTION OF THE INVENTION

Figure 2A:
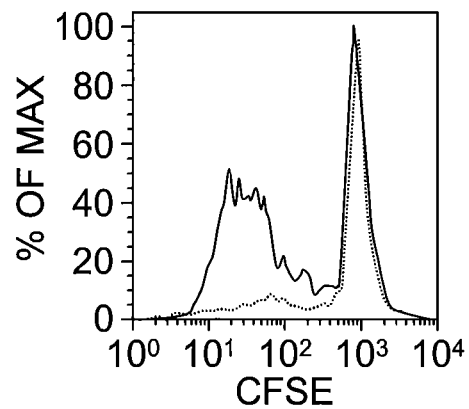
FIG. 2 shows MILTENYI bead-purified, CFSE-labeled peripheral T cells stimulated with aAPCs coated with agonistic antibodies to CD3 (100 ng/ml, FIG. 2A), or CD3/CD28 (100 ng/ml, FIG. 2B; 0.5/100 ng/ml, FIG. 2C), for 5 days, in the presence of 20 µg/ml of either blocking anti-PILAR antibodies (dotted line) or an irrelevant rabbit antibody (solid line). These results are representative of 4 independent experiments.

A novel human transmembrane ligand for CD161 has now been identified. This protein, designated Proliferation-Induced Lymphocyte-Associated Receptor (PILAR) is up-regulated upon early T cell activation and can both enhance TCR-dependent stimulation through CD161 and induce apoptotic T cell death through a second receptor. The results disclosed herein reveal a crucial role for PILAR in modulating the extent of cellular adaptive immune responses in humans. Accordingly, the present invention relates to a nucleic acid molecule encoding PILAR, PILAR polypeptide, anti-PILAR antibodies, PILAR agonists and antagonists, and methods for using such molecules to modulate immune responses in the treatment of cancer, autoimmune diseases or inflammation.

In accordance with the present invention, an isolated nucleic acid molecule encoding a PILAR polypeptide is intended to include a genomic DNA, RNA or cDNA encoding the PILAR polypeptide or fragment thereof. The nucleic acid molecule is isolated in the sense that the molecule is separated or substantially free from at least some of the other components of the naturally occurring organism, such as for example, the cell structural components or other polypeptides or nucleic acids commonly found associated with the molecule.

In one embodiment, the nucleic acid molecule encodes a PILAR polypeptide having the amino acid sequence as set forth in SEQ ID NO:1. In another embodiment, the nucleic acid molecule encodes a PILAR polypeptide having the amino acid sequence as set forth in SEQ ID NO:9. In a particular embodiment the nucleic acid molecule has a nucleotide sequence as set forth in SEQ ID NO:6. In still other embodiments, the nucleic acid molecule of the present invention hybridizes to a nucleic acid molecule encoding a PILAR polypeptide of SEQ ID NO:1 or SEQ ID NO:9, or nucleic acid molecule as set forth in SEQ ID NO:6 under stringent conditions. In accordance with this embodiment, stringent hybridization is carried by conducting the hybridization reaction at 42° C. in a solution containing 50% formamide, 5×SSC, and 1% SDS and washing at 65° C. in a solution containing 0.2×SSC and 0.1% SDS See, e.g., Sambrook et al., *Molecular Cloning, A Laboratory Manual* (2d Ed. 1989) (Cold Spring Harbor Laboratory).

Alternatively stated, the isolated nucleic acid molecules of the invention encompass nucleic acid molecules encoding PILAR polypeptides that have at least about 85%, 90%, 95%, 97%, 98% or higher amino acid sequence identity across the entire length of the polypeptide sequences specifically disclosed herein and, in some embodiments, further encode a functional PILAR polypeptide as defined herein.

As is known in the art, a number of different programs can be used to identify whether a nucleic acid molecule or polypeptide has sequence identity or similarity to a known sequence. Sequence identity and/or similarity can be determined using standard techniques known in the art, including, but not limited to, the local sequence identity algorithm of Smith & Waterman (1981) *Adv. Appl. Math.* 2:482, by the sequence identity alignment algorithm of Needleman & Wunsch (1970) *J. Mol. Biol.* 48:443, by the search for similarity method of Pearson & Lipman (1988) *Proc. Natl. Acad. Sci. USA* 85:2444, by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux, et al. (1984) *Nucl. Acid Res.* 12:387-395, either using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle (1987) *J. Mol. Evol.* 35:351-360; the method is similar to that described by Higgins & Sharp (1989) *CABIOS* 5:151-153.

Another example of a useful algorithm is the BLAST algorithm, described in Altschul, et al. (1990) *J. Mol. Biol.* 215: 403-410 and Karlin, et al. (1993) *Proc. Natl. Acad. Sci. USA* 90:5873-5787. A particularly useful BLAST program is the WU-BLAST-2 program which was obtained from Altschul, et al. ((1996) *Methods in Enzymology*, 266:460-480). WU-BLAST-2 uses several search parameters, which can be set to the default values. The parameters are dynamic values and are established by the program itself depending upon the composition of the particular sequence and composition of the particular database against which the sequence of interest is being searched; however, the values can be adjusted to increase sensitivity. An additional useful algorithm is gapped BLAST as reported by Altschul, et al. ((1997) *Nucleic Acids Res.* 25:3389-3402).

A percentage amino acid sequence identity value can be determined by the number of matching identical residues divided by the total number of residues of the longer sequence in the aligned region. The longer sequence is the one having the most actual residues in the aligned region (gaps introduced by WU-Blast-2 to maximize the alignment score are ignored).

The alignment can include the introduction of gaps in the sequences to be aligned. In addition, for sequences which contain either more or fewer amino acids than the polypeptides specifically disclosed herein, it is understood that in one embodiment, the percentage of sequence identity will be determined based on the number of identical amino acids in relation to the total number of amino acids. Thus, for example, sequence identity of sequences shorter than a sequence specifically disclosed herein, will be determined using the number of amino acids in the shorter sequence, in one embodiment. In percent identity calculations relative weight is not assigned to various manifestations of sequence variation, such as, insertions, deletions, substitutions, etc.

For the purposes of the present invention, a functional PILAR polypeptide is one that retains at least one biological activity normally associated with this polypeptide, e.g., binding to CD161 and/or stimulating T cell activation or proliferation. Alternatively, a functional PILAR polypeptide retains all of the activities possessed by the unmodified peptide. By retains biological activity, it is meant that the polypeptide retains at least about 50%, 60%, 75%, 85%, 90%, 95%, 97%, 98%, 99%, or more, of the biological activity of the native polypeptide (and can even have a higher level of activity than the native polypeptide). A non-functional polypeptide is one that exhibits essentially no detectable biological activity normally associated with the polypeptide (e.g., at most, only an insignificant amount, e.g., less than about 10% or even 5%).

A PILAR polypeptide or PILAR protein as used herein, is intended to be construed broadly and encompasses a protein capable of binding CD161 and enhancing CD3/CD28-dependent T cell proliferation and cytotoxic T cell activation. In one embodiment, the PILAR polypeptide contains a transmembrane domain near the N-terminus of the polypeptide, and has an overall length of about 120 to about 190 amino acid residues. In particular embodiments, the length of the polypeptide is about 174 amino acid residues. In some embodiments, the polypeptide has a C-terminal amino acid sequence as set forth in SEQ ID NO:9. In other embodiments, the PILAR polypeptide can be defined as having or lacking the intracellular and transmembrane domains. In accordance with certain aspects of this embodiment, the PILAR polypeptide encompasses the C-terminal 124 amino acid residues of SEQ ID NO:1.

The term PILAR polypeptide also includes a modified (e.g., mutated) PILAR that retains biological function (i.e., have at least one biological activity of the native PILAR polypeptide, e.g., binding to CD161), and functional PILAR fusion polypeptides (e.g., a PILAR-GST protein fusion or a PILAR-His tagged protein).

To modify the PILAR amino acid sequence specifically disclosed herein, amino acid substitutions can be based on any characteristic known in the art, including the relative similarity or differences of the amino acid side-chain substituents, for example, their hydrophobicity, hydrophilicity, charge, size, and the like. In particular embodiments, conservative substitutions (i.e., substitution with an amino acid residue having similar properties) are made in the amino acid sequence encoding PILAR.

In making amino acid substitutions, the hydropathic index of amino acids may be considered. The importance of the hydropathic amino acid index in conferring interactive biologic function on a protein is generally understood in the art (see, Kyte and Doolittle (1982) *J. Mol. Biol.* 157:105). It is accepted that the relative hydropathic character of the amino acid contributes to the secondary structure of the resultant protein, which in turn defines the interaction of the protein with other molecules, for example, enzymes, substrates, receptors, DNA, antibodies, and the like.

Each amino acid has been assigned a hydropathic index on the basis of its hydrophobicity and charge characteristics (Kyte and Doolittle (1982) supra), and these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is also understood in the art that the substitution of amino acids can be made on the basis of hydrophilicity. U.S. Pat. No. 4,554,101 states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (±3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

As will be appreciated by those skilled in the art, there can be variability in the nucleic acid molecules that encode any one of the PILAR polypeptides disclosed herein due the addition of regulatory sequences (e.g., non-translated sequences, such as intronic sequences and 5'- and 3'-untranslated sequences, promoters, enhancers, and the like) and the degeneracy of the genetic code. The degeneracy of the genetic code, which allows different nucleic acid sequences to code for the same polypeptide, is well-known in the literature (see Table 1).

TABLE 1

| Amino Acid | 3-Letter Code | 1-Letter Code | Codons |
|---|---|---|---|
| Alanine | Ala | A | GCA GCC GCG GCT |
| Cysteine | Cys | C | TGC TGT |
| Aspartic acid | Asp | D | GAC GAT |
| Glutamic acid | Glu | E | GAA GAG |
| Phenylalanine | Phe | F | TTC TTT |
| Glycine | Gly | G | GGA GGC GGG GGT |
| Histidine | His | H | CAC CAT |
| Isoleucine | Ile | I | ATA ATC ATT |
| Lysine | Lys | K | AAA AAG |
| Leucine | Leu | L | TTA TTG CTA CTC CTG CTT |
| Methionine | Met | M | ATG |
| Asparagine | Asn | N | AAC AAT |
| Proline | Pro | P | CCA CCC CCG CCT |
| Glutamine | Gln | Q | CAA CAG |
| Arginine | Arg | R | AGA AGG CGA CGC CGG CGT |
| Serine | Ser | S | AGC ACT TCA TCC TCG TCT |
| Threonine | Thr | T | ACA ACC ACG ACT |
| Valine | Val | V | GTA GTC GTG GTT |
| Tryptophan | Trp | W | TGG |
| Tyrosine | Tyr | Y | TAC TAT |

As indicated, the nucleic acid molecule encoding PILAR can also be associated with appropriate expression control sequences, e.g., transcription/translation control signals and polyadenylation signals to regulate transcription and translation of the PILAR polypeptide. It will be appreciated that a variety of promoter/enhancer elements can be used depending on the level and tissue-specific expression desired. The promoter can be constitutive or inducible (e.g., the metallothionein promoter or a hormone inducible promoter), depending on the pattern of expression desired. The promoter can be native or foreign and can be a natural or a synthetic sequence. By foreign, it is intended that the transcriptional initiation region is not found in the wild-type host into which the transcriptional initiation region is introduced. The promoter is chosen so that it will function in the target host cell(s) of interest. In particular embodiments, the promoter functions in immune cells (e.g., T cells including CD4$^+$ and CD8$^+$ T cells and APCs such as dendritic cells, macrophages, or B cells) or in cells that can be used to express nucleic acid molecules encoding PILAR for the purposes of large-scale protein production. Likewise, the promoter can be specific for certain cells and tissues in that PILAR is only expressed in these cells or tissues. In some embodiments, the PILAR coding sequence is operatively associated with the well-known cytomegalovirus (CMV) major immediate-early promoter, albumin promoter, Elongation Factor 1-α (EF1-α) promoter, PγK promoter, MFG promoter, Rous sarcoma virus promoter, or glyceraldehyde-3-phosphate promoter.

PILAR can be expressed not only directly, but also as a fusion protein with a heterologous polypeptide, i.e. a signal sequence for secretion and/or other polypeptide which will aid in the purification of PILAR. In one embodiment, the heterologous polypeptide has a specific cleavage site to remove the heterologous polypeptide from PILAR.

In general, a signal sequence can be a component of the vector and should be one that is recognized and processed (i.e., cleaved by a signal peptidase) by the host cell. For production in a prokaryote, a prokaryotic signal sequence from, for example, alkaline phosphatase, penicillinase, or heat-stable enterotoxin II leaders can be used. For yeast secretion, one can use, e.g., the yeast invertase, alpha factor, or acid phosphatase leaders, the *Candida albicans* glucoamylase leader (EP 362,179), or the like (see, for example WO 90/13646). In mammalian cell expression, signal sequences from secreted polypeptides of the same or related species, as well as viral secretory leaders, for example, the herpes simplex glycoprotein D signal can be used.

Other useful heterologous polypeptides which can be fused to PILAR include those which increase expression or solubility of the fusion protein or aid in the purification of the fusion protein by acting as a ligand in affinity purification. Typical fusion expression vectors include those exemplified herein as well as pMAL (New England Biolabs, Beverly, Mass.) and pRIT5 (Pharmacia, Piscataway, N.J.) which fuse maltose E binding protein or protein A, respectively, to the target recombinant protein.

The nucleic acid molecule encoding PILAR can be incorporated into a vector, e.g., for the purposes of cloning or other laboratory manipulations, recombinant protein production, or gene delivery. In particular embodiments, the vector is an expression vector. By the term express, expresses or expression of a nucleic acid coding sequence, in particular a PILAR coding sequence, it is meant that the sequence is transcribed, and optionally, translated. Typically, according to the present invention, transcription and translation of the coding sequence will result in production of a PILAR polypeptide.

Generally, vectors of the present invention include bacterial artificial chromosomes, cosmids, yeast artificial chromosomes, phage, plasmids, lipid vectors and viral vectors (e.g., retrovirus, alphavirus, vaccinia virus, adenovirus, adeno-associated virus, or herpes simplex virus), wherein the choice of vector is made based on a number of factors known in the art, including age and species of the target host cell, in vitro vs. in vivo delivery, level and persistence of expression desired (e.g., transient or stable), intended purpose (e.g., for therapy or drug screening), the target cell or organ, route of delivery, size of the isolated nucleic acid molecule, safety concerns, and the like.

For example, for expression of PILAR in the yeast *S. cerevisiae*, vectors such as pYepSec1 (Baldari, et al. (1987) *EMBO J.* 6:229-234), pMFa (Kurjan and Herskowitz (1982) *Cell* 30:933-943), pJRY88 (Schultz, et al. (1987) *Gene* 54:113-123), and pYES2 (INVITROGEN Corporation, San Diego, Calif.) can be employed. Baculovirus vectors available for expression of nucleic acids to produce proteins in cultured insect cells (e.g., Sf9 cells) include the pAc series (Smith, et al. (1983) *Mol. Cell. Biol.* 3:2156-2165) and the pVL series (Lucklow and Summers (1989) *Virology* 170:31-39). Examples of mammalian expression vectors include pCDM8 (Seed (1987) *Nature* 329:840) and pMT2PC (Kaufman, et al. (1987) *EMBO J.* 6:187-195). When used in mammalian cells, the expression vector's control functions are often provided by viral regulatory elements. For example, commonly used promoters are derived from polyoma, adenovirus 2, cytomegalovirus and Simian Virus 40. When expressing in a mammalian subject is desired, viral vectors are generally employed.

As used herein, the term viral vector or viral delivery vector can refer to a virus particle that functions as a nucleic acid delivery vehicle, and which contains the vector genome packaged within a virion. Alternatively, these terms can be used to refer to the vector genome when used as a nucleic acid delivery vehicle in the absence of the virion. Protocols for producing recombinant viral vectors and for using viral vectors for nucleic acid delivery can be found in *Current Protocols in Molecular Biology*, Ausubel, F. M. et al. (eds.) Greene Publishing Associates, (1989) and other standard laboratory manuals (e.g., Vectors for Gene Therapy. In: *Current Protocols in Human Genetics*. John Wiley and Sons, Inc.: 1997). See also, Muzyczka et al. (1992) *Curr. Topics Micro. Immunol.* 158:97-129; U.S. Pat. No. 6,146,874; and Miller (1990) *Blood* 76:271.

The present invention also provide for delivering, and optionally expressing, a nucleic acid molecule encoding PILAR in a broad range of host cells, including both dividing and non-dividing cells in vitro (e.g., for large-scale recombinant protein production or for use in screening assays) or in vivo (e.g., for recombinant large-scale protein production, for creating an animal model for disease, or for therapeutic purposes). Vectors can be introduced into prokaryotic or eukaryotic cells via conventional transformation or transfection techniques. As used herein, the terms transformation and transfection refer to a variety of art-recognized techniques for introducing foreign nucleic acids (e.g., DNA) into a host cell, including calcium phosphate or calcium chloride co-precipitation, DEAE-dextran-mediated transfection, lipofection, electroporation, microinjection, DNA-loaded liposomes, LIPOFECTAMINE-DNA complexes, cell sonication, gene bombardment using high velocity microprojectiles, and viral-mediated transfection. Suitable methods for transforming or transfecting host cells can be found in Sambrook, et al. (Molecular Cloning: A Laboratory Manual, 2nd Edition, Cold Spring Harbor Laboratory press (1989)), and other laboratory manuals.

Often only a small fraction of cells (in particular, mammalian cells) integrate the foreign DNA into their genome. In order to identify and select these integrants, a nucleic acid molecule that encodes a selectable marker (e.g., resistance to antibiotics) can be introduced into the host cells along with the nucleic acid of interest. In particular embodiments, selectable markers include those that confer resistance to drugs, such as G418, hygromycin and methotrexate. Nucleic acids encoding a selectable marker can be introduced into a host cell on the same vector as that comprising the nucleic acid of interest or can be introduced on a separate vector. Cells stably transfected with the introduced nucleic acid molecule can be identified by drug selection (e.g., cells that have incorporated the selectable marker gene will survive, while the other cells die).

Host cells for use in screening assays or recombinant PILAR protein production can be a bacterial, protozoan, plant, yeast, fungus, or animal cell. In one embodiment, the cell is an animal cell (e.g., insect, avian or mammalian), and in another embodiment a mammalian cell (e.g., an immune cell such as an APC). In particular embodiments, an isolated nucleic acid molecule encoding PILAR is introduced into a cultured cell, e.g., a cell of a primary or immortalized cell line for recombinant protein production. The recombinant cell is used to produce the PILAR polypeptide, which is collected from the cells or cell culture medium. Likewise, recombinant protein can be produced in, and optionally purified from an organism (e.g., a microorganism, animal or plant) being used essentially as a bioreactor.

Thus, the present invention also provides a transgenic non-human animal containing an isolated nucleic acid molecule encoding PILAR, which can be produced according to methods well-known in the art. The transgenic non-human animal can be any species, including avians and non-human mammals. In accordance with the invention, suitable non-human mammals include mice, rats, rabbits, guinea pigs, goats, sheep, pigs and cattle. Mammalian models for cancer and autoimmune diseases can also be used.

A nucleic acid encoding PILAR is stably incorporated into cells within the transgenic animal (typically, by stable integration into the genome or by stably maintained episomal constructs). It is not necessary that every cell contain the transgene, and the animal can be a chimera of modified and unmodified cells, as long as a sufficient number of cells contain and express the PILAR transgene so that the animal is a useful screening tool (e.g., so that administration of test agents give rise to detectable response).

Methods of making transgenic animals are routinely practiced in the art. DNA constructs are introduced into the germ line of an avian or mammal to make a transgenic animal. For example, one or several copies of the construct can be incorporated into the genome of an embryo by standard transgenic techniques. In an exemplary embodiment, a transgenic non-human animal is produced by introducing a transgene into the germ line of the non-human animal. Transgenes can be introduced into embryonal target cells at various developmental stages. Different methods are used depending on the stage of development of the embryonal target cell.

Introduction of the transgene into the embryo can be accomplished by any of a variety of means known in the art such as microinjection, electroporation, lipofection or a viral vector. For example, the transgene can be introduced into a mammal by microinjection of the construct into the pronuclei of the fertilized mammalian egg(s) to cause one or more copies of the construct to be retained in the cells of the developing mammal(s). Following introduction of the transgenic construct into the fertilized egg, the egg can be incubated in vitro for varying amounts of time, or reimplanted into the surrogate host, or both. One common method is to incubate the embryos in vitro for about 1-7 days, depending on the species, and then reimplant them into the surrogate host. The progeny of the transgenically manipulated embryos can be tested for the presence of the construct (e.g., by Southern blot analysis) of a segment of tissue. An embryo having one or more copies of the exogenous cloned construct stably integrated into the genome can be used to establish a permanent transgenic animal line carrying the transgenically added construct. Methods of producing transgenic avians are also known in the art, see, e.g., U.S. Pat. No. 5,162,215.

When it is desirable to produce large amounts of PILAR protein, generally the PILAR protein is recombinantly produced and purified. When PILAR is expressed in a recombinant cell other than one of human origin, the PILAR is completely free of proteins or polypeptides of human origin. However, it may be necessary to purify PILAR from recombinant host cell proteins or polypeptides to obtain preparations that are substantially homogeneous as to PILAR. As a first step, the culture medium or cell lysate is centrifuged to remove particulate cell debris. The membrane and soluble protein fractions are then separated. PILAR can then be purified from the soluble protein fraction. PILAR thereafter can then be purified from contaminant soluble proteins and polypeptides with, for example, the following suitable purification procedures: by fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; gel filtration using, for example, SEPHADEX G-75; ligand affinity chromatography, and protein A SEPHAROSE columns to remove contaminants such as IgG.

Whether purified or expressed by a recombinant host cell, the PILAR polypeptide of the present invention can be used in screening assays for identifying antagonists and agonists of PILAR. Cell-free screening assays generally involve contacting purified PILAR (e.g., in the presence or absence of CD161) with a test agent and determining whether the test agent binds and/or modulates an activity of PILAR as compared to a PILAR polypeptide which has not been contacted with the test agent. Test agents in the cell-free assay can be synthesized or otherwise affixed to a solid substrate, such as plastic pins, glass slides, plastic wells, and the like. Further, isolated PILAR can be free in solution, affixed to a solid support, or expressed on a cell surface for conducing cell-free screening assays. Alternatively, a PILAR fusion protein can be provided to facilitate binding of PILAR to a matrix. For example, glutathione-S-transferase fusion proteins can be adsorbed onto glutathione SEPHAROSE beads (Sigma Chemical, St. Louis, Mo.) or glutathione-derivatized microtitre plates, which are then combined with the test agent, and the mixture incubated under conditions conducive to complex formation (e.g., at physiological conditions for salt and pH). Such cell-free screening assays can be used to identify PILAR agonists, which mimic or stimulate binding of PILAR to CD161 or other alternative receptor, as well as PILAR antagonists, which block binding of PILAR to CD161 or other alternative receptor. In this regard, it is contemplated that PILAR agonists and PILAR antagonists can bind to either CD161 or PILAR.

In an alternative embodiment, a PILAR agonist or antagonist is identified in a cell-based assay. The steps involved in this screening assay of the invention include, contacting a test cell which expresses a recombinant PILAR polypeptide with a test agent, and determining the whether the test agent modulates an activity of PILAR. Activities of PILAR which can be assayed in accordance with this screening method include binding of PILAR to CD161 or other alternative receptor, proliferation or activation of T cells (e.g., naïve or cytotoxic T cells), expression of IL-10, or surface expression of CD28, as compared to a control cell (e.g., a cell not contacted with the test agent). Such cell-based screening assays can be used to identify PILAR agonists, which mimic or stimulate binding of PILAR to CD161 or other alternative receptor, or increase expression of PILAR. Likewise, such cell-based screening assays can be used to identify PILAR antagonists, which block binding of PILAR to CD161 or other alternative receptor or inhibit the expression of PILAR.

While the cell-based assay can be carried out using any suitable cell including bacteria, yeast, insect cells (e.g., with a baculovirus expression system), avian cells, mammalian cells, or plant cells, in particular embodiments, the test cell is a mammalian cell (e.g., an APC). Screening assays can also be carried out in vivo in animals. Cells modified to express a recombinant PILAR can be transiently or stably transformed with the nucleic acid molecule encoding PILAR. Stably transformed cells can be generated by stable integration into the genome of the organism or by expression from a stably maintained episome (e.g., Epstein Barr Virus derived episomes). The test cells of the screening method of the invention can be cultured under standard conditions of temperature, incubation time, optical density, plating density and media composition corresponding to the nutritional and physiological requirements of the cells. However, conditions for maintenance and growth of the test cell can be different from those for assaying candidate agents in the screening methods of the invention. Any techniques known in the art can be applied to establish the optimal conditions.

Screening assays of the invention can be performed in any format that allows rapid preparation and processing of multiple reactions such as in, for example, multi-well plates of the 96-well variety. Stock solutions of the agents as well as assay components are prepared manually and all subsequent pipetting, diluting, mixing, washing, incubating, sample readout and data collecting is done using commercially available robotic pipetting equipment, automated work stations, and analytical instruments for detecting the output of the assay.

In addition to the reagents provided above, a variety of other reagents can be included in the screening assays of the invention. These include reagents like salts, neutral proteins, e.g., albumin, detergents, etc. Also, reagents that otherwise improve the efficiency of the assay, such as protease inhibitors, nuclease inhibitors, anti-microbial agents, and the like can be used.

Test agents which can be screened in accordance with the methods of the present invention are generally derived from libraries of agents or compounds. Such libraries can contain either collections of pure agents or collections of agent mixtures. Examples of pure agents include, but are not limited to, proteins, antibodies, aptamers, polypeptides, peptides, nucleic acids, oligonucleotides, siRNA, carbohydrates, lipids, synthetic or semi-synthetic chemicals, and purified natural products. Examples of agent mixtures include, but are not limited to, extracts of prokaryotic or eukaryotic cells and tissues, as well as fermentation broths and cell or tissue culture supernates. In the case of agent mixtures, the methods of this invention are not only used to identify those crude mixtures that possess the desired activity, but also provide the means to monitor purification of the active agent from the mixture for characterization and development as a therapeutic drug. In particular, the mixture so identified can be sequentially fractionated by methods commonly known to those skilled in the art which can include, but are not limited to, precipitation, centrifugation, filtration, ultrafiltration, selective digestion, extraction, chromatography, electrophoresis or complex formation. Each resulting subtraction can be assayed for the desired activity using the original assay until a pure, biologically active agent is obtained.

Additional screens, such as well-established computational screens, are also contemplated for use in conjunction with the screening method disclosed herein. Such screens could employ using the agents disclosed herein as lead compounds for the generation of libraries of compounds which modulate the activity of PILAR.

Exemplary agents of the instant invention include antagonistic and agonist antibodies which specifically bind to PILAR and modulate T cell proliferation. Such antibodies can be either polyclonal or monoclonal. Moreover, such antibodies can be natural or partially or wholly synthetically produced. All fragments or derivatives thereof (e.g., Fab, Fab', F(ab')$_2$, scFv, Fv, or Fd fragments) which maintain the ability to specifically bind to and recognize PILAR are also included. The antibodies can be a member of any immunoglobulin class, including any of the human classes: IgG, IgM, IgA, IgD, and IgE.

The PILAR-specific antibodies can be generated using classical cloning and cell fusion techniques. See, for example, Kohler and Milstein (1975) *Nature* 256:495-497; Harlow and Lane (1988) Antibodies: A Laboratory Manual, Cold Spring Harbor Laboratory, New York. Alternatively, antibodies which specifically bind PILAR are derived by a phage display method. Methods of producing phage display antibodies are well-known in the art (e.g., Huse, et al. (1989) *Science* 246 (4935):1275-81).

Selection of PILAR-specific antibodies is based on binding affinity and can be determined by various well-known immunoassays including, enzyme-linked immunosorbent, immunodiffusion chemiluminescent, immunofluorescent, immunohistochemical, radioimmunoassay, agglutination, complement fixation, immunoelectrophoresis, and immunoprecipitation assays and the like which can be performed in vitro, in vivo or in situ. Such standard techniques are well-known to those of skill in the art (see, e.g., "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. (1984) *J. Clin. Chem. Clin. Biochem.* 22:895-904).

Once fully characterized for specificity, the antibodies of the invention can be assayed for their ability to agonize or antagonize binding of PILAR to CD161 or other alternative receptor via techniques such as ELISA, co-immunoprecipitation experiments and the like.

PILAR agonists and PILAR antagonists (collectively referred to hereafter as agents) identified in accordance with the assay methods of the present invention, as well as vectors, nucleic acids, and PILAR polypeptides disclosed herein (collectively referred to hereafter as molecules) will be useful in various applications including modulating T cell proliferation and activation, surface levels of CD28 and Th1 cytokine secretion. Such method generally involve contacting an immune cell, such as an antigen presenting cell, with an agent or molecule that increases or decreases the expression or activity (including binding to CD161) of PILAR so that T cell proliferation or activation, surface levels of CD28 or Th1 cytokine secretion is modulated. Methods for analyzing these responses are well-known in the art and disclosed herein. In particular embodiments, an agent or molecule that blocks PILAR expression or activity or the PILAR-CD161 interaction is used to decrease T cell proliferation or activation, lower surface levels of CD28 and decrease Th1 cytokine secretion; whereas an agent or molecule that increases PILAR expression or activity or the PILAR-CD161 interaction is used to stimulate T cell proliferation or activation, increase surface levels of CD28 and increase Th1 cytokine secretion.

In so far as the molecules and agents of the invention ultimately modulate CD161 activity, the prevent invention also relates to methods stimulating and decreasing immune responses in a subject. Such methods involve administering to a subject in need of treatment an effective amount of an agent or molecule disclosed herein thereby stimulating or decreasing immune responses in the subject. In most cases the subject being treated will be a human being, but treatment of agricultural animals, e.g., livestock and poultry, and companion animals, e.g., dogs, cats and horses, is expressly covered herein. The dosage or effective amount of an agent or molecule is an amount which achieves the desired outcome of reducing at least one sign or symptom of a disease or disorder involving CD161 activity. By way of illustration, PILAR antagonists can be used to ameliorate symptoms in autoimmune disease (e.g., diabetes mellitus type 1, systemic lupus erythematosus, Sjögren's syndrome, Hashimoto's thyroiditis, Graves' disease, and rheumatoid arthritis) or inflammation by preventing the activation of autoreactive T cells via PILAR. Conversely, PILAR agonists can be used to mimic PILAR signaling to improve the anti-tumor immune response resulting from tumor-specific T cell activation.

To evaluate the efficacy of any one of these molecules or agents of this invention, one of skill will appreciate that a model system of any particular disease or disorder involving CD161 activity can be utilized to evaluate the adsorption, distribution, metabolism and excretion of a compound as well as its potential toxicity in acute, sub-chronic and chronic studies.

For therapeutic use, it is generally desirable that the agents and molecules of the present invention be provided to a subject in a pharmaceutically acceptable carrier and at an appropriate dose. Such pharmaceutical compositions can be prepared by methods and contain carriers which are well-known in the art. A generally recognized compendium of such methods and ingredients is Remington: The Science and Practice of Pharmacy, Alfonso R. Gennaro, editor, 20th ed. Lippincott Williams & Wilkins: Philadelphia, Pa., 2000. A pharmaceutically acceptable carrier, composition or vehicle, such as a liquid or solid filler, diluent, excipient, or solvent encapsulating material, is involved in carrying or transporting the subject compound from one organ, or portion of the body, to another organ, or portion of the body. Each carrier must be acceptable in the sense of being compatible with the other ingredients of the formulation and not injurious to the subject being treated.

Examples of materials which can serve as pharmaceutically acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other nontoxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Pharmaceutical compositions appropriately formulated for parenteral (for example, by intravenous, intraperitoneal, subcutaneous or intramuscular injection), topical (including buccal and sublingual), oral, intranasal, intravaginal, or rectal administration can be prepared according to standard methods.

The selected dosage level will depend upon a variety of factors including the activity of the particular agent or molecule employed, the route of administration, the time of administration, the rate of excretion or metabolism of the particular agent being employed, the duration of the treatment, other drugs, compounds and/or materials used in combination with the particular agent employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of an agent at levels lower than that required in order to achieve the desired therapeutic effect and gradually increase the dosage until the desired effect is achieved. Moreover, given the efficacy antibodies and of an VEGFR1 siRNA developed by Sirna Therapeutics (San Francisco, Calif.) for the treatment of AMD, one of skill in the art can appreciate dosing of such molecules useful for achieving the desired therapeutic result with no systemic or local adverse events.

The invention is described in greater detail by the following non-limiting examples.

Example 1

Materials and Methods

Tissues and Cells. Tissues were obtained and single-cell suspensions were prepared by gently forcing minced fresh specimens through a 70 µm-pore mesh and subjected to FICOLL gradient centrifugation. Peripheral blood lymphocytes were obtained by leukopheresis/elutriation and MILTENYI bead-purified (Conejo-Garcia, et al. (2004) *Cancer Res* 64:2175-2182). DCs were generated by incubating magnetically purified $CD14^+$ cells for 7 days with Granulocyte-macrophage colony stimulating factor (20 ng/ml; PEPROTECH, Rocky Hill, N.J.) and IL-4 (50 ng/ml; R&D Systems, Minneapolis, Minn.).

Immunohistochemistry was performed using anti-CD161 monoclonal antibodies (DX12 and B199.2) and the ABC kit (CHEMICON, Temecula, Calif.). Horse serum (1/10 dilution) was used as a negative control.

K562 cells were transduced with CD32 according to established methods (Maus, et al. (2002) *Nat. Biotechnol.* 20:143-148). Expression of CD161 and PILAR was achieved with the pLENTI6/V5-D-TOPO lentiviral system (INVITROGEN, Carlsbad, Calif.). 293 cells were stably transfected with a pCEFL-kz plasmid encoding Hemagglutinin (HA)-PILAR. Artificial APCs (aAPCs) were gamma-irradiated (100 Gy), washed and loaded with anti-CD3 (OKT3; eBioscience, San Diego, Calif.) or anti-CD3 plus ati-CD28 (15E8; CHEMICON, Temecula, Calif.) antibodies at room temperature. T cells were added at a 10:1 ratio. $A2^+$ aAPCs were generated by transducing K562 cells with lentiviral human CD80 and HLA-A*0201. Positive cells were selected by FACS sorting.

Antibodies and cytokines. Flow cytometry was performed using anti-CD8 (OKT8), anti-CD28 (CD28.2), anti-CD45RA (HI100), anti-CD80 (2D10.4) and anti-CD62L (DREG56) antibodies from eBioscience; anti-CCR7 (3D12) and anti-CD3 (SP34-2) antibodies from BD Biosciences; anti-CD161 (B199.2) and anti-HLA-A2 (BB7.2) from Serotec (Raleigh, N.C.); and custom rabbit polyclonal anti-PILAR antibody plus anti-rabbit Ig-FITC (Biomeda, Foster City, Calif.). Cytokines in supernatants from stimulated T cells were quantified in a BIO-PLEX assay (BIO-RAD, Hercules, Calif.) using the Human-27-Plex panel. Plates were read in a BIO-PLEX Array Reader (BIO-RAD).

Immunoprecipitation and Immunoblotting. K562 cells transduced with CD161 and 293T cells stably transfected with HA-PILAR were lysed on ice for 45 minutes at 4° C. in 500 µl of lysis buffer (50 mM Tris-Cl, pH 7.5, 15 mM EDTA, 100 mM NaCl, 0.1% (w/v) TRITON X-100, 1 mM dithiothreitol and 1 mM PEFABLOC SC (Roche, Manheim, Germany). The lysates were incubated on ice for 90 minutes with 20 μl anti-CD-161 (DX12) or 3 μl anti-HA (HA.11; Covance, Berkeley, Calif.) monoclonal antibodies, or an irrelevant rabbit IgG (NeoMarkers, Fremont, Calif.). Following centrifugation at 13,000×g for 10 minutes at 4° C., the supernatants were incubated with 25 μl Protein G/protein A-agarose beads (CALBIOCHEM, San Diego, Calif.) for 45 minutes at 4° C. with continuous rotation and washed (30 seconds, 1000 g). Pellets were resuspended in 30 μl Laemmli buffer, boiled, loaded onto a 15% SDS-PAGE, transferred to a nitrocellulose membrane, blocked and incubated with the indicated primary antibody. Immunoreactive bands were developed using horseradish peroxidase-conjugated secondary antibodies (BIO-RAD, Hercules, Calif.) and chemiluminescent substrate (Pierce, Rockford, Ill.).

Characterization of Genomic, cDNA and Amino Acid Sequences of PILAR. The predicted amino acid sequence of the following genes encoding a C-type Lectin domain (Smart #00034 of the EMBL database) were aligned with ClustalW software to create a pattern with the residues conserved in at least 6 of 9 sequences and coded by a single exon: AF097358, AF461811, AY486-483, Z22576, AF175206, AY358499, DQ049594, HSA133532 and AF133299.

Genomic sequences at chromosome 12p12-13 were translated into the 6 possible ORFs by using ORF Finder software and were scanned for the presence of the pattern with PattinProt software.

RACE-PCR was performed with the human spleen marathon-ready cDNA kit (CLONTECH, Carlsbad, Calif.), following manufacturer's instructions. The following internal primers were used:

```
Forward.Outer:
                                 (SEQ ID NO: 10)
5'-CAG GGG ACT GGC TTG GAG TGA GAG AT-3';

Forward.Inner:
                                 (SEQ ID NO: 11)
5'-TCT GAT GAT ACC AGA AAT TGG ACA GCC AGT-3';

Reverse.Outer:
                                 (SEQ ID NO: 12)
5'-ATG GGC CCT CAC CAG AGG TTC CGT AT-3';

Reverse.Inner:
                                 (SEQ ID NO: 13)
5'-TGC TGC AAA TCC ACT TGA TAT CAA TAA A-3'.
```

Generation of an Anti-PILAR Antibody. The structure of PILAR was predicted with RASMOL software. Based on a putative structural similarity, a good matching of cysteines and the absence of high content of gaps, a CD69-like fold was assigned to the new sequence. A rabbit polyclonal antibody was generated against a fragment of PILAR located on a region of the extracellular domain not conserved on structurally related molecules. Moreover, this region putatively forming a β-strand at the C-terminus (Ser-Phe-Ala-Phe-Leu-Ser-Ala-Asp-Gly-Val-His-Ser- Ser-Arg-Gly-Phe-Ile-Asp-Ile-Lys;. SEQ ID NO: 14)

Real-Time Quantitative PCR. PILAR expression was analyzed by TAQMAN PCR analysis according to established methods (Boyman, et al. (2006) Science 311:1924-1927; Poggi, et al. (1998) Eur. J. Immunol. 28:1611-1616; Currier, et al. (2002) J. Immunol. Methods 260:157-172). PILAR expression was analyzed with the following primers: PILAR.F, 5'-GTT AGC GCC TTG CCA TGA TTA-3' (SEQ ID NO:15); PILAR.R, 5'-AGG AAG CAC ATA AGG CCA ATC TT-3' (SEQ ID NO:16); and the probe PILAR.P, 5'-(FAM)CTT CAT ACA TCG GAT AGT TCC CAA GTT GAT ACA(TAMRA)-3' (SEQ ID NO:17). The cDNA load was normalized to human glyceraldehyde-3-phosphate dehydrogenase (GAPDH) with primers GAPDH F: 5'-CCT GCA CCA CCA ACT GCT TA-3' (SEQ ID NO:18) and GAPDH R: 5'-CAT GAG TCC TTC CAC GAT ACC A-3' (SEQ ID NO:19) and the probe GAPDH.P: 5'-(FAM)CCT GGC CAA GGT CAT CCA TGA CAA C (TAMRA)-3' (SEQ ID NO:20).

Generation of Soluble Fusion Proteins. The cDNAs that encode the extracellular domains of PILAR (124 amino acid residues) and CD161 (160 amino acid residues) were PCR amplified from mRNA isolated from human spleen using the primer sets PILAR.F: 5'-aag ctt AAG CAT GCT AAA CCT GTG GCA TGT TC-3' (SEQ ID NO:21); PILAR.R: 5'-gaa ttc AAA ATA TTT AGG TTT GCT GCA AAT C-3' (SEQ ID NO:22); and CD161.F: 5'-aag ctt ATA CAG AAA TCA TCA ATA GAA AAA TGC-3' (SEQ ID NO:23); CD161.R: 5'-gga tcc GAG TCA GGA TAC ACT TTA TTT CTC ACA-3' (SEQ ID NO:24), respectively, which introduced restriction sequences for HindIII and EcoRI (PILAR) and for HindIII and BamHI (CD161). The fragments were subcloned into pSecTag (INVITROGEN) in-frame with a human Ig leader sequence (upstream) and a Myc epitope (downstream), followed by a 6×His-tag, to generate the constructs Ig-PILAR-Myc and Ig-CD161-Myc. The sequence amplified with primers BTN.F: 5'-aag ctT CAG TTT TCT GTG CTT GGA C-3' (SEQ ID NO:25) and BTN.R: 5'-gaa ttc TCT GGG CGC TCC TGA AGA AG-3' (SEQ ID NO:26), corresponding to the extracellular domain of BTN3A1 (GENBANK Accession No. NM_007048) was cloned, expressed and purified in the same manner and used as a negative control.

293 cells were independently transfected with the plasmids pIg-PILAR-Myc, pIg-CD161-Myc and pIg-BTN-Myc using LIPOFECTAMINE (INVITROGEN), following manufacturer's instructions. Supernatants from the 2 transfections were harvested at day 3 and 7 and the secreted fusion proteins were purified from culture medium by using a standard Ni column (GE Healthcare), following manufacturer's instructions. After dialysis against PBS, protein concentration was determined by the Bradford assay.

ELISPOT Analysis. For ELISPOT analysis, $2\times10^6$ PBMCs/ml from an A2$^+$ donor were incubated for 7 days (10:1) ratio with CEF peptide pool-pulsed (2 μg/ml) A2$^+$ aAPCs or autologous monocyte-derived dendritic cells (generated by incubating magnetically purified CD14$^+$ cells for 7 days with Granulocyte-macrophage colony stimulating factor (20 ng/ml, PEPROTECH) and IL-4 (50 ng/ml, R&D Systems)). Interferon-γ ELISPOT was performed on day 8 against irradiated A2$^+$ aAPCs or autologous monocyte-derived dendritic cells (10:1 ratio), pulsed with 2 μg/mL antigens.

Flat-bottomed, 96-well nitrocellulose-lined plates (Millipore MultiScreen, Millipore, Bedford, Mass.) were coated with IFN-γ monoclonal antibody (MD-1; eBioscience, San Diego, Calif.) and incubated overnight at 4° C. After washing with Coating Buffer (eBioscience, San Diego, Calif.), plates were blocked with 10% FBS serum for 2 hours at 37° C. Effector and target cells were incubated together for 20 hours in RPMI medium 1640 supplemented with 10% FBS. After incubation, the plates were thoroughly washed with 0.05% TWEEN 20 in PBS to remove cells, and biotinylated secondary IFN-γ monoclonal antibody (4S.B3; eBioscience) was added to each well. After incubation for 2 hours at 37° C., the plates were washed and developed with Avidin-horseradish peroxidase (eBioscience) for 1 hour at room temperature. After washing, fresh substrate (3-amino-9-ethyl carbazole; Sigma, St. Louis, Mo.) was added and the plates incubated for approximately 20 minutes.

Example 2

Identification PILAR

Amino acid sequence alignment of known or predicted molecules mapping at chromosome 12p12-p13 and exhibiting a C-type Lectin domain was conducted. The alignment revealed the identification of the conserved pattern Cys-Pro-(Xaa)$_2$-Trp-(Xaa)$_2$-[Tyr-Phe]-(Xaa)$_3$-Cys-Tyr-(Xaa)$_2$-Ser-(Xaa)$_5$-Trp-(Xaa)$_2$-Ser-(Xaa)$_3$-Cys (SEQ ID NO:7), wherein Xaa is any amino acid residue. This motif was used to screen the genomic sequences (~2 Mb) mapping at the human chromosome 12p12-p13, translated in their six possible open reading frames. A continuous genomic sequence was identified and was found to encode an amino acid sequence with 74% amino acid sequence identity with this aforementioned pattern (Cys-Ser-Gly-Asp-Trp-Leu-Gly-Val-Arg-Asp-Lys-Cys-Phe-Tyr-Phe-Ser-Asp-Asp-Thr-Arg-Asn-Trp-Thr-Ala-Ser-Lys-Ile-Phe-Cys (SEQ ID NO:8). This 29 amino acid sequence was found on a provisional GENBANK mRNA entry identified as C-type lectin domain family 2, member (CLEC2A; Accession Number: NM_207375). However, because the entire open reading frame of the identified genomic clone could not be PCR-amplified from cDNA derived from five different leukocyte subsets, including human B cells, T cells, NK cells, dendritic cells or monocytes, it was concluded that the identified clone corresponds to a splice variant which differed from CLEC2A. To identify a corresponding mRNA for the genomic clone, a leukocyte-specific cDNA library was created by RACE-PCR with cDNA from human spleen. The full-length cDNA sequence of the newly identified gene had five exons encoding a transmembrane molecule containing a truncated extracellular C-type lectin-like domain (FIG. 1A). As depicted in FIG. 1B, sequence similarity searches identified the immunoreceptors CD69 and CLEC2D/LLT1 as two closely-related human molecules. Moreover, as shown in FIG. 1C, the protein shares 100% amino acid sequence identity with the N-terminal 137 amino acid residues of CLEC2A and INPE5792 (GENBANK Accession No. AAQ89483), but is divergent from these protein in the remaining 37 amino acid residues, i.e., Phe-Glu-Ile-Ile-Gly-Asn-Gly-Ser-Phe-Ala-Phe-Leu-Ser-Ala-Asp-Gly-Val-His-Ser-Ser-Arg-Gly-Phe-Ile-Asp-Ile-Lys-Trp-Ile-Cys-Ser-Lys-Pro-Lys-Tyr-Phe-Leu (SEQ ID NO:9). The predicted amino acid sequence of this novel protein identifies the presence of a short cytoplasmic domain and a truncated C-type Lectin domain (FIG. 1D).

Example 3

PILAR is a Ligand for the CD161 Immunoreceptor

Real-Time Q-PCR analysis showed that, in addition to spleen, the novel sequence was constitutively expressed on human thymus and small intestine, indicating that this protein may be expressed in lymphocytes. Consequently, PCR analysis showed the mRNA signal in T and B cells, but not on epithelial tumor cell lines. In addition, lower mRNA levels were detected in the genital tract (i.e., testis and ovary), where lymphocyte numbers are low. No detectable expression was found in any other tissue tested (e.g., breast, brain, liver, muscle, or colon). The highest expression of the new protein was identified on CD8$^+$ T cells, followed by B lymphocytes and CD4$^+$ T cells. No detectable mRNA levels were found on myeloid leukocytes or natural killer (NK) cells.

Because of the homology with CLEC2D/LLT1, the only known ligand for CD161, it was contemplated that the new molecule could also bind to CD161. To demonstrate this interaction, 293 cells were stably transfected with a construct encoding the novel sequence fused in-frame with a hemagglutinin epitope at the 5'-end (i.e., the novel sequence was inserted into the pCEFL-kz plasmid (Crespo, et al. (1997) Nature 385:169-172)). Likewise, CD161 was transduced into K562 cells using a pLXSN retrovirus encoding CD161 and selected with neomycin. Lysates from both lines were then incubated for 2 hours and immunoprecipitation was performed separately with an anti-hemagglutinin antibody (HA11, Covance, Berkeley, Calif.) or an anti-CD161 antibody in the presence of protein G/protein A agarose beads. Western blot analysis revealed that lysates immunoprecipitated with anti-hemagglutinin antibodies contained a ~40 kD band reacting with the anti-CD161 antibody, while immunoprecipitation with anti-CD161 allowed the detection of a ~20 kD band that reacted with the anti-hemagglutinin antibody. No band was detectable when CD161-expressing K562 cells were incubated with the parental 293 cells, or when 293 cells expressing the novel sequence were incubated with plain K562 cells. In different experiments, it was confirmed that the anti-CD161 antibody reacted with the expected ~40 kD band only when the lysates were immunoprecipitated with the anti-hemagglutinin antibody, but not when the immunoprecipitation was performed with an irrelevant antibody. Therefore, the novel transmembrane molecule binds specifically to CD161.

Confirming the PILAR/CD161 interaction, a soluble chimeric CD161-Myc epitope protein, but not an irrelevant-Myc protein, specifically bound to K562 cells ectopically expressing PILAR and not the PILAR-K562 cell line. Moreover, a chimeric PILAR protein specifically bound to CD161-transduced K562 cells. Together, these data demonstrate that the novel transmembrane molecule interacts with CD161.

Example 4

Transient Up-Regulation of PILAR on Activated Lymphocytes

Based on the similarities with CD69, it was surmised that expression of the novel protein disclosed herein could be transiently up-regulated upon lymphocyte activation (Sancho, et al. (2005) Trends Immunol. 26:136-140). To demonstrate this, peripheral CD8$^+$ T cells ($10^6$) were isolated and incubated with phytohemagglutinin (PHA; 10 µg/mL) for different periods of time. The new CD161 ligand was maximally up-regulated at 9 hours after activation of peripheral T cells, with the mRNA message decreasing thereafter. Comparable results were found with CD4$^+$ T cells.

To verify this pattern of up-regulation after CD3/CD28-dependent stimulation, a previously-described artificial antigen-presenting cell (aAPC) system was employed (Conejo-Garcia, et al. (2004) supra; Conejo-Garcia, et al. (2003) supra; Maus, et al. (2002) Nat. Biotechnol. 20:143-148). Briefly, the method involves the use of (MHC-1 deficient) K562 cells transduced with CD32, which can subsequently be coated with agonistic CD3 and CD28 antibodies (100 ng/mL). Consistent with the up-regulation upon stimulation with PHA, CD3/CD28 activation also induced a maximum over-expression of the new CD161 ligand at 9 hours, with a dramatic decrease compared to constitutive mRNA levels found on naïve lymphocytes after T cell activation for more than 20 hours. Based on this expression pattern and the presence of a transmembrane domain, the new CD161 ligand was designated Proliferation-Induced Lymphocyte-Associated Receptor (PILAR).

FACS analysis performed with an endotoxin-free PILAR-specific antibody confirmed that PILAR surface expression was detectable in less than 2% of naïve T cells. However, after CD3/CD28-stimulation for three days, PILAR became detectable on CD4 T cells and reached a maximum level on both proliferating CD4 and CD8 T cells (but not in cells that did not proliferate) at day 7. Similar uncoupled mRNA and protein expression are frequently observed on primed T cells, as they initially undergo translational attenuation (Cham, et al. (2003) *J. Biol. Chem.* 278:17044-17052; Scheu, et al. (2006) *Nat. Immunol.* 7:644-651; Mao, et al. (1992) *J. Biol. Chem.* 267:20444-20450). Correspondingly, a rapid PILAR mRNA degradation was found shortly after T cell activation; PILAR mRNA was nearly undetectable at 45 minutes after actinomycin D treatment. In agreement with previous reports, CD161 was not found on naïve T cells, but it was clearly detectable on both CD4 and CD8 T cells upon CD3/CD28 stimulation.

Example 5

PILAR Enhances TCR-Mediated Proliferation of Human T Cells

Since PILAR was quickly up-regulated on early activated T cells, the effect of increased PILAR availability on T cell proliferation was determined by ectopically expressing PILAR on the PILAR$^-$ aAPCs. To define activating conditions of different stringency, a proliferation assay was performed using decreasing concentrations of anti-CD3 mAb (500 ng-0.5 pg/ml), and a constant concentration of 100 ng/ml of anti-CD28 monoclonal antibody. Based on 5-day proliferation analysis of naive T cells, concentrations of anti-CD3 of 100 ng/ml and 0.5 ng/ml were defined as "optimal" and "limiting", respectively. Hence, under optimal TCR-stimulation conditions but in the absence of CD28 signaling, ectopic PILAR dramatically enhanced the proliferation of naïve T cells (53% increase in total proliferating cells). Because co-stimulatory molecules prevent the induction of apoptosis by increasing Bcl-xL (Sperling, et al. (1996) *J. Immunol.* 157:3909-3917), expression was next compared on T cells stimulated with agonistic CD3 antibodies in the presence or the absence of PILAR. Results of this analysis indicated that increasing PILAR availability augmented Bcl-xL levels and, to a much lesser extent, c-FLIP, after 24 hours of stimulation. Together, these data indicate that PILAR enhances the expansion of TCR-stimulated T cells by increasing their survival through enhanced expression of anti-apoptotic proteins. Of note, PILAR appears not to be expressed by myeloid cells indicated that, in vivo, T cells present PILAR to each other for engagement to CD161 in a reciprocal manner. Similar T-T co-stimulatory interactions occur between CD27 and CD70 (Huang, et al. (2006) *J. Immunol.* 176:7726-7735), although they appear to be more relevant for secondary responses (Watts (2005) *Annu. Rev. Immunol.* 23:23-68; Borst, et al. (2005) *Curr. Opin. Immunol.* 17:275-281).

Figure 3A:
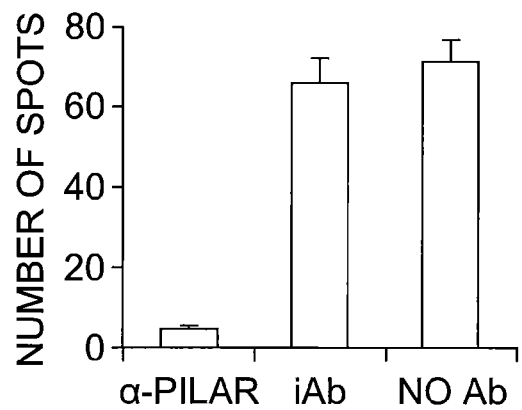
FIG. 3A shows IFN-γ ELISPOT analysis of PBMCs from an A2$^+$ donor, stimulated for 7 days with A2$^+$CD80$^+$ aAPCs (10:1 ratio) pulsed with the CEF peptide pool (MABTECH, 2 µg/mL of each peptide), in the presence of 20 µg/ml of anti-PILAR (α-PILAR) or an irrelevant antibody (iAb).
Figure 3B:
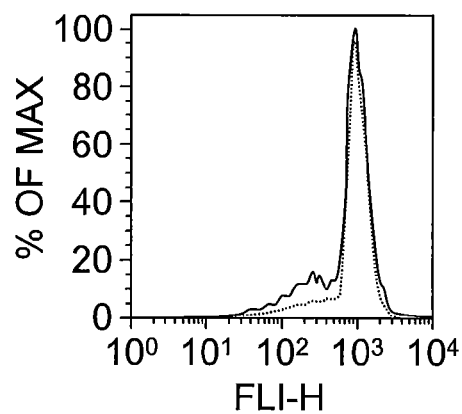
FIG. 3B shows 2×10$^6$ CFSE-labeled PBMCs/ml incubated for 7 days with the CEF peptide pool (1.75 µg/ml) in the presence of 20 µg/ml of anti-PILAR antibodies (dashed line) or an irrelevant antibody (solid line).
Figure 3C:
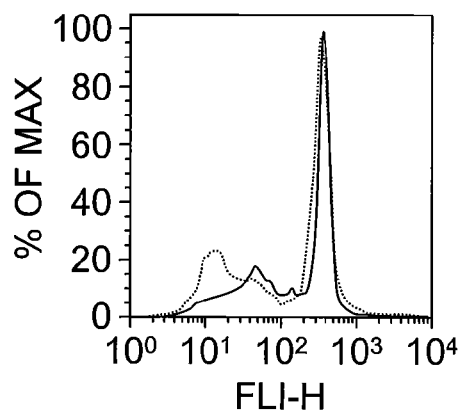
FIG. 3C shows PBMCs stimulated for 7 days with autologous monocyte-derived dendritic cells (10:1 ratio, 10$^6$ total cells/ml), pulsed with pool of 138 Cytomegalovirus peptides (2 µg/mL; pp 65 sequence, strain AD169; BD Biosences), in the presence of 20 µg/ml of anti-PILAR (dotted line) or an irrelevant antibody (solid line).

Significantly, PILAR overexpression profoundly increased the production of IFN-γ and the IFN-responsive chemokine CXCL10 by stimulated T cells (FIG. 3C). Similarly, the inflammatory chemokines CCL3, CCL4 and CCL5, as well as GM-CSF, which increases the production of myeloid cells, were dramatically upregulated by ectopic PILAR signaling. In contrast, PILAR had no effect on CXCL8 or G-CSF secretion. These results indicate a fine balance between activation and inhibition that regulates T cell homeostasis. IL-12 strongly upregulates CD161 expression on NK cells (Poggi, et al. (1998) *Eur. J. Immunol.* 28:1611-1616), and CD161 signaling, in turn, induces the secretion of IFN-γ.

Example 6

PILAR/CD161 Interactions are Critical for CD3-Mediated Proliferation

Paradoxically, increased PILAR availability in the presence of CD3 plus CD28 signaling decreased T cell proliferation. It was contemplated that PILAR enhances T cell proliferation through CD161 under suboptimal activating conditions and triggers an alternative regulatory pathway through a different receptor in vigorously activated lymphocytes. To demonstrate this, human naïve T cells were activated under optimal CD3 stimulation conditions in the absence or the presence of ectopic PILAR and anti-CD161 antibodies. Strikingly, in the presence of ectopic PILAR, >37% lymphocytes underwent apoptosis when an anti-CD161 antibody, but not a control Ig, was added to the media, as indicated by annexin V staining. Apoptosis was initiated within 24 hours of T cell activation and also occurred in naïve T cells exposed to PILAR expressed on the aAPCs. The presence of the anti-CD161 antibody did not result in detectable apoptosis or cell death in the absence of ectopic PILAR, ruling out a direct cytotoxic effect. These data indicate that PILAR induces T cell apoptosis through a second receptor present on naïve T cells that is upregulated shortly after TCR-stimulation, and that this apoptotic cell death is prevented by the engagement of CD161. Since PILAR decreases the proliferation of CD3/CD28 co-stimulated T cells, it is believed that this alternative receptor is also upregulated upon CD28 signaling.

Collectively, these results point to a model whereby PILAR, depending on the receptor preferentially expressed at different stages of T cell activation, either increases T cell survival through CD161, or induces apoptotic death through a different mediator.

Example 7

PILAR Blockade Abrogates the Expansion of Both CD4 and CD8 T Cells

Figure 2B:
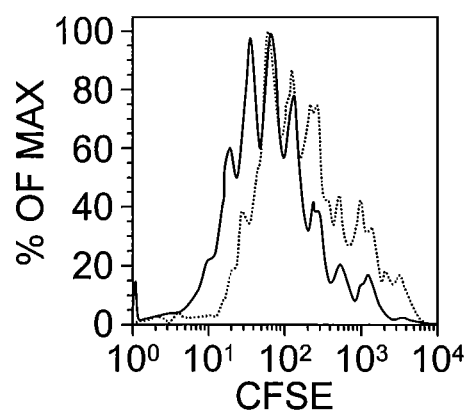
Figure 2C:
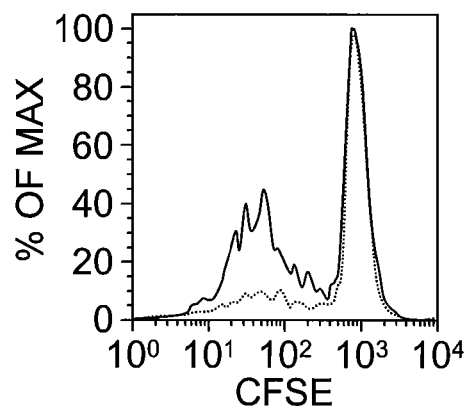

To further demonstrate the critical role of PILAR on T cell proliferation, it was determined whether PILAR blockade affected TCR-mediated signaling. In the presence of anti-PILAR antibodies, the CFSE signal of magnetically purified T cells expanded under optimal conditions of CD3 stimulation was significantly lower than the signal from cells that were incubated with an irrelevant Ig. Furthermore, this signal was comparable to that of unstimulated lymphocytes (FIG. 2). A high level of co-stimulation (anti-CD28 at 100 ng/ml) was required to rescue the inhibition of proliferation mediated by PILAR blockade, although a decrease in the strong CD3/CD28-mediated expansion was still apparent. Comparable results were obtained with higher concentrations of plate-bound antibody. Under limiting conditions of TCR engagement, a dramatic impairment of proliferation was observed after the addition of an anti-PILAR antibody, even in the presence of co-stimulation (FIG. 2C). Additionally, PILAR blockade abrogated the generation of IFN-γ-secreting, antigen-specific HLA-A2 CD8 T cells responding to a cocktail of 23 immunogenic, class I restricted 8-11mers (Currier, et al. (2002) *J. Immunol. Methods* 260:157-172) presented by A2+ aAPCs or autologous dendritic cells (FIG. 3A), as well as the proliferation of peripheral blood mononuclear cells (PBMCs) induced by these specific antigens (FIG. 3B). Addition of anti-PILAR antibodies also impaired the proliferation of CD4 and CD8 T cells induced by autologous DCs pulsed with 138 different Cytomegalovirus 15-mers with 11 amino acid overlaps (FIG. 3C). These data confirm that endogenous PILAR, depending on the relative strength of the TCR signal and the degree of co-stimulation, is critical for the proliferation of naïve T cells.

Notably, a reduction in the surface expression of CD28 was observed when naïve T cells were stimulated with CD3/CD28 for 2 days in the presence of anti-PILAR antibody, compared to cells cultured with an irrelevant antibody. A major decrease in the expression of surface CD62L, which mediates lymphocyte homing during inflammation, was also observed upon PILAR blockade. A comparable decrease was observed at day 7 and when lymphocytes were activated through PHA in the presence or the absence of anti-PILAR antibody. Taken together, these results indicate that, in vivo, PILAR modulates the capacity of T lymphocytes to home to lymph nodes through CD62L, where they can undergo a robust expansion in the presence of increased CD28 signaling.

In addition, incubation of purified naïve T cells with anti-PILAR antibodies in the absence of TCR stimulation resulted in the up-regulation of IL-10 at both the mRNA and protein levels, compared to lymphocytes incubated with identical concentrations of an irrelevant antibody. No significant effect on the expression of TGF-β was observed, whereas a 50% decrease in the levels of interferon-γ was detected. These data indicate that 2% of naïve T cells expressing PILAR can also regulate the production of cytokines such as IL-10 under resting conditions through autocrine and paracrine interactions.

Example 8

CD3/CD28 Signaling Recovers PILAR and CD161 Expression on Human Tumor-Infiltrating T Cells A majority of the T cells isolated from human tumors have an effector memory phenotype (Broderick, et al. (2006) *Clin. Immunol.* 118:159-169). Since the expression of CD161 in healthy donors identifies mostly T cells with effector memory differentiation (Takahashi, et al. (2006) supra), rather than natural killer (NK) T cells, it was contemplated that the tumor microenvironment could prevent the anti-tumor immune response by down-regulating the expression of the PILAR/CD161 pair on tumor-infiltrating T cells.

To demonstrate this effect, it was first confirmed that >92% CD8 T cells present in single-cell suspensions prepared from seven different human ovarian carcinoma specimens exhibited a CCR7−CD69−CD45RA+/− (effector memory) phenotype, although some specimens contained a small proportion of naïve T cells, ranging from 3 to 7%. The great majority of these cells were negative for the early activation marker CD69, which is expressed transiently by fully activated effector T cells. They did not express the invariant (Vα24-JαQ) TCR chain, indicating that, unlike other cancer types (Terabe, et al. (2006) *Cancer Res.* 66:3869-3875), NK T cells do not play a significant role in the physiopathology of established ovarian carcinomas. Although a significant infiltration of CD161+ cells were observed in both the stroma and the tumor islets of most specimens analyzed, CD161 was found on less than 1% of CD8 T cells by flow cytometry. In contrast, variable levels of CD161 were found on autologous tumor-derived CD4 T cells. As CD161 expression in healthy donors is mostly found on effector memory cells (Takahashi, et al. (2006) *J. Immunol.* 176:211-216), these data indicate that CD161-mediated stimulation is specifically abrogated by the tumor microenvironment on effector T cells. Furthermore, most tumors contained CD4 and CD8 tumor-infiltrating T cells that expressed PILAR, indicating that CD4+ lymphocytes, which include CD25+Foxp3+ regulatory T cells (Sato, et al. (2005) *Proc. Natl. Acad. Sci. USA* 102:18538-18543), may be more susceptible to PILAR-mediated expansion. In contrast, CD8+ lymphocytes, the only cell type known to exert immune pressure against ovarian cancer growth (Sato, et al. (2005) supra), may be prone to PILAR-mediated apoptotic death.

Figure 4A:
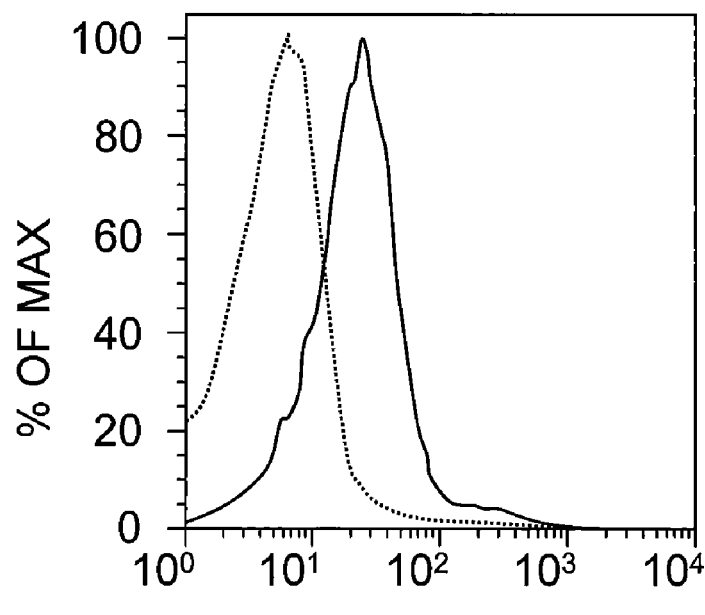
FIG. 4 shows that the expression of both PILAR (FIG. 4A) and CD161 (FIG. 4B) can be recovered on tumor-associated cytotoxic T cells ex vivo by activation with aAPCs. The gate was on CD3$^+$CD8$^+$ cells. Dotted line, tumor-derived unstimulated CD8$^+$ T cells; solid line, the same cells after stimulation with CD3/CD28 for 5 days.
Figure 4B:
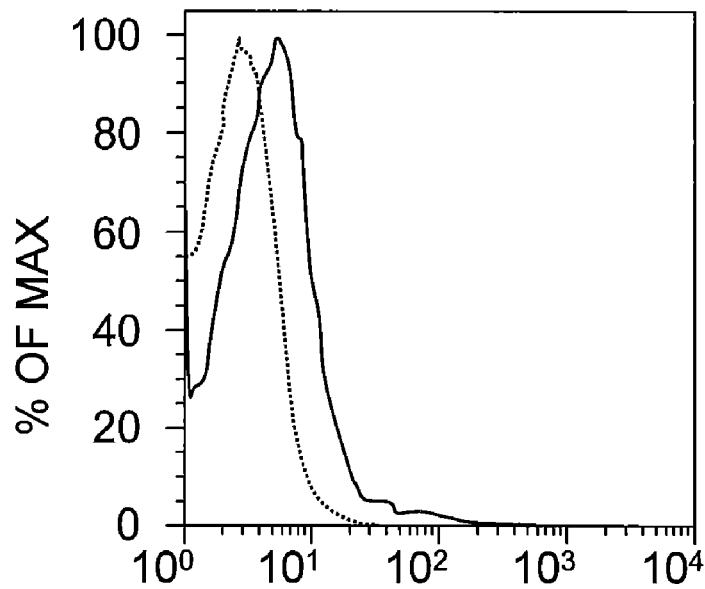

Importantly, CD3/CD28-mediated T cell stimulation resulted in a significant upregulation of surface CD161 on CD8 T cells (FIG. 4A). These data indicate that anti-tumor T cells can be recovered from tumor-induced immunosuppression ex vivo and converted into activated cytotoxic cells with a strong proliferative capacity. The observation that the expression of PILAR on CD8 T cells increased dramatically upon activation supports this conclusion (FIG. 4B). In summary, PILAR represents a crucial modulator of the extent of cellular immune responses in humans. The results provide a mechanistic rationale for the manipulation of PILAR signaling, which may unveil new interventions against autoimmunity, inflammation and cancer.

What is claimed is:

1. A method for identifying an agent which modulates an activity of Proliferation-Induced Lymphocyte-Associated Receptor (PILAR) comprising contacting a PILAR polypeptide comprising SEQ ID NO:9, or host cell expressing a PILAR polypeptide comprising SEQ ID NO:9, with a test agent and determining whether the test agent modulates an activity of PILAR, wherein the activity is:

(a) binding of PILAR to CD161;
(b) proliferation of a T cell;
(c) activation of a T cell; or
(d) surface expression of CD28, wherein a decrease in a PILAR activity is indicative of an agent which antagonizes PILAR and an increase in PILAR activity is indicative of an agent which agonizes PILAR.

* * * * *

UNITED STATES PATENT AND TRADEMARK OFFICE
CERTIFICATE OF CORRECTION

PATENT NO. : 8,084,217 B2  
APPLICATION NO. : 12/595093  
DATED : December 27, 2011  
INVENTOR(S) : Conejo-Garcia et al.

Page 1 of 1

It is certified that error appears in the above-identified patent and that said Letters Patent is hereby corrected as shown below:

In the Specification

Column 1, please delete Lines 13-16 and insert in its place the following:
--This invention was made with government support under grant numbers RR016437 and P20 RR016437 awarded by the National Institutes of Health. The government has certain rights in the invention.--

Signed and Sealed this  
Twenty-eighth Day of April, 2020

Andrei Iancu  
*Director of the United States Patent and Trademark Office*